United States Patent [19]

Ericsson et al.

[11] Patent Number: 5,068,089
[45] Date of Patent: Nov. 26, 1991

[54] KIT FOR TESTING HUMAN MALES FOR FERTILITY

[75] Inventors: Ronald J. Ericsson; Scott A. Ericsson, both of Alzada, Mont.

[73] Assignee: Androscore Corporation, Alzada, Mont.

[21] Appl. No.: 660,081

[22] Filed: Feb. 25, 1991

Related U.S. Application Data

[60] Division of Ser. No. 404,467, Sep. 8, 1989, which is a continuation-in-part of Ser. No. 242,104, Sep. 9, 1988, abandoned.

[51] Int. Cl.$^5$ .................... G01N 33/50; G01N 21/78
[52] U.S. Cl. .......................... 422/61; 422/58; 422/102; 422/82.08; 422/82.09; 436/808; 436/180
[58] Field of Search ................ 436/1, 65, 165, 166, 436/172, 180, 800, 808, 906; 422/55, 58, 61, 82.08, 82.09, 102; 435/31

[56] References Cited

U.S. PATENT DOCUMENTS 3,909,363 9/1975 Bucalo ...................... 195/103.5 R Primary Examiner—David L. Lacey
Assistant Examiner—David Redding
Attorney, Agent, or Firm—Millen, White & Zelano

[57] ABSTRACT

The potential fertility of a semen sample is evaluated using a kit comprising a collection tube with volume gradients on its side; a funnel which is fitted into the collection tube for guiding an ejaculate into the collection tube; a pipet containing a standard aqueous solution of the dye resazurin stored therein for metering a predetermined amount of the solution into the collection tube; and insulating sleeve for surrounding a glass containing hot water and the collection tube and for maintaining the water at an elevated temperature for a predetermined period of time, and a color chart ranging in color from the color of the semen sample and dye solution mixture immediately after mixing to the color of a corresponding mixture of the dye solution and a highly fertile semen sample, after being maintained at the same elevated temperature for the same period of time. Alternatively, for clinical laboratory use, the sample may be examined by a spectrophotometer, colorometer, fluorescent microscope or fluorometer in lieu comparing the mixture to a color chart.

8 Claims, 3 Drawing Sheets

1

KIT FOR TESTING HUMAN MALES FOR FERTILITY

This is a division of U.S. application Ser. No. 07/404,467, filed Sept. 8, 1989, as a continuation-in-part application of U.S. application Ser. No. 07/242,104, filed Sept. 9, 1988, now abandoned.

BACKGROUND OF THE INVENTION

This invention relates to a kit to be used in testing human male semen for potential fertility. More particularly, this invention relates to a kit for testing human male fertility by in vitro testing of sperm metabolism in a semen sample.

Generally, tests which provide an assessment of the potential fertility of sperm are ordered through a physician. This can be a relatively expensive procedure since one must visit the physician's office and pay the physician's fee as well as lab fees. If a man is undergoing treatment for infertility, repeated trips to the physician's office for testing adds expense as well as inconvenience to the procedure. In addition, there are individuals who are hesitant to seek treatment from a physician because they have no objective basis for requesting treatment. If an individual, in the privacy of his home, can at least preliminarily assess objectively the potential fertility of his sperm, many of the shortcomings associated with current test methods can be avoided. While providing for self-testing is important, it is also useful to provide a more convenient approach for laboratory testing of sperm samples wherein the tests can be conducted utilizing relatively inexpensive, readily available equipment.

In conventional sperm analysis, in which sperm count and sperm motility are the primary factors, there are no strict threshold levels separating fertility from infertility, except in the situation wherein there are no moving sperm, which is always associated with infertility. A sperm count of twenty million sperm per milliliter or greater is generally considered to be in the fertile range, whereas a lower count is considered subfertile. There is some disagreement on this in that some laboratories and clinicians use rates of thirty million sperm per milliliter or forty million sperm per milliliter as the fertility threshold. These values are not fixed in that it has been determined that twenty percent of human males with counts below twenty million sperm per milliliter will father children and as many as fifteen percent of human males with normal sperm counts may have some degree of sperm dysfunction due to other reasons which interfere with fertility. A sperm specimen with normal sperm count or with normal sperm motility does not invariably establish fertility in that individual. In addition, there is disagreement as to what constitutes the lower limit of sperm motility that can be considered normal or fertile, with estimates ranging between forty to sixty percent of the sperm in a given sample. In summary, sperm analysis is not one hundred percent accurate and in characterizing human male patients as fertile or infertile, the accuracy of the characterization is generally less than ninety percent.

It has been found that a measurement of human male fertility is the collective metabolism rate of the sperm in an ejaculate. Such a measurement takes into consideration both sperm count and sperm motility, which provides a basis for calculating the proportion of the total sperm population theoretically capable of fertilizing the ovum.

While resazurin, as well as methylene blue, have been used to test the potential fertility of bovine semen samples, there has been no indication that resazurin could be used effectively in testing semen samples of human males for potential fertility because generally, bull semen has much higher sperm densities than human semen, e.g., on the order of one billion sperm per milliliter for a fertile bull, in contrast to 70 to 100 million sperm per milliliter for a fertile human male. Also, the research on bull semen tested the rate at which the dye became pink or colorless, a technique not readily adaptable to use in a kit intended primarily for home testing, and most, if not all, of the bull ejaculates were fertile and the objective of the testing was to measure the degree of fertility rather than attempting to distinguish between fertile and sub-fertile or infertile ejaculates. The use of resazurin for bovine semen analysis is set forth in R. E. Erb et al., "Resazurin Reducing Time as an Indicator of Bovine Semen Fertility Capacity", *Journal of Dairy Science*, page 853, December 1950 and R. E. Erb et al., "Modified Resazurin Reduction Test for Estimating Fertility Capacity of Bull Semen", *Journal of Dairy Science*, page 881, 1952. The utilization of resazurin for testing bull semen has its origins in the use of resazurin as a reagent in testing milk.

SUMMARY OF THE INVENTION

It is an object of the present invention to provide a kit for assessing the potential fertility of sperm which does not separately require determining sperm motility and sperm count. Another object is to provide a method of conducting such a test at home or in a laboratory.

In view of the aforementioned objects and other objects, the instant invention contemplates a method of assessing the potential fertility of the sperm in a semen sample in accordance with one embodiment of the invention by visually observing the extent to which reducible dye mixed with the semen sample is reduced so as to change the color of the dye. The color or shade which the dye assumes after it has been exposed to the metabolic processes of the sperm in the semen sample for a finite period of time is then matched to color standards on a color chart in order to visually assess the potential fertility of the sperm in the semen sample.

The potential fertility of sperm in a viable semen sample is a function of both sperm count and sperm motility, both of which are directly related to the collective metabolism rate of the total population of sperm in the semen sample. Therefore, the ability of the sperm to reduce a dye is a measure of human male potential fertility.

In accordance with a second embodiment of the invention, the semen sample is mixed with a reducible dye and examined with a spectrophotometer. Semen samples of insufficient count and motility to reduce the dye have an absorbency different from semen samples of a count and motility sufficient to reduce the dye. Alternatively, a colorometer may be used instead of a spectrophotometer.

In accordance with a third embodiment of the invention, the semen sample is examined for fluorescence with a fluorescent microscope or a fluorometer after being mixed with dye. If the dye is reduced or is being reduced, indicating sufficient sperm count and motility, substantial fluorescence either occurs or can be induced. If reduction of the dye does not occur or is minimal, indicating low sperm count and motility, fluorescence is nonexistent or minimal.

In a method aspect, this invention relates to a method of mixing a measured volume of a semen sample with a predetermined amount of a dye capable of being reduced. In the presence of metabolizing sperm, the dye can change from an initial color to a second color. The amount of dye mixed with the semen sample is coordinated with the volume of the semen sample so that a maximum change in color state will be achieved in the dye solution-semen sample mixture if the semen sample is potentially maximally fertile and a minimal or no color change if the sperm sample has decreased or no potential fertility. The method further contemplates maintaining the dye-semen sample at a temperature and/or a period of time which a color change is affected by a corresponding mixture of the dye and semen sample known to be highly fertile; and thereafter, in accordance with the first embodiment of the invention, comparing the color of the mixture of the semen sample and the dye with a color chart comprising at least one color corresponding to a color produced by a semen sample known to be highly fertile, when mixed with the same amount of dye. In accordance with a second embodiment of the invention, the mixture is examined with a spectrophotometer or color meter to determine absorbance of light and, in accordance with a third embodiment of the invention, the mixture is examined for fluorescence with a fluorescent microscope or fluorometer.

In a kit aspect, this invention relates to a test kit for determining the potential fertility of a semen sample, the test kit comprising:

a container with collection means for receiving the semen sample, comprising a gradation thereon for determining the volume of the semen sample;

a dispensing device for dispensing a measured amount of dye capable of being reduced in the presence of metabolizing sperm from one colored state to another colored state;

means for maintaining the mixture of dye and semen sample at an elevated temperature; and a color chart comprising a plurality of color samples corresponding to the color change affected in corresponding mixtures of the dye and sperm samples of known varying sperm count and sperm motility including an infertile sperm sample.

DETAILED DISCUSSION

The semen employed in the method of this invention is preferably a freshly collected ejaculate. However, because the loss in viability of sperm after storage whether at room temperature, refrigerator temperature or liquid nitrogen temperature, is well known, this loss in viability can be dealt with by an appropriate adjustment in the fertility score assigned to the sample based on the color change affected by the stored sample in the kit described herein below.

The preferred dye in accordance with the instant invention is resazurin (also known as diazoresorcinol), which in its unreduced state imparts a deep purple, dark blue or black color to aqueous solutions thereof. The test according to the invention is performed by mixing an appropriate amount of the dye with the sperm sample, i.e., in a preselected ratio, and permitting the mixture to stand at a temperature at which the semen metabolizes, which is then matched with standards on a color chart having at least one color chip thereon which is indicative of a selected level of reduction of the dye due to the collective metabolism of sperm in a selected volume of semen.

Typically, the color chart will have a first color chip whose color corresponds to the color of the starting dye immediately after being with the aforesaid selected volume of semen, i.e., prior to any reduction of the dye. This color chip is identified on the chart as the "infertile" color chip, i.e., if no color change occurs, there is an insufficient number of metabolizing viable sperm in the semen sample to achieve a measurable amount of reduction of the dye. A second color chip, identified as the "fertile" color chip, has a color corresponding to the maximum color change achievable with a sperm sample of the same volume containing a typically maximum number of motile sperm, i.e., whose collective metabolizing rate is the maximum. The ratio of dye to volume of semen is selected so that the maximum color or shade change is achieved with such a semen sample. Additional color chips are also present on the color chart whose colors or shades are intermediate between the first and second color chips to provide gradient standards between the "fertile" and "infertile" color chips.

Alternatively, the kit can contain only one color chip, which corresponds to the color change achieved with a minimally fertile ejaculate, e.g., one which contains about 20 million motile sperm per milliliter. If the color change achieved with the test ejaculate is less than the color of this standard color chip, the instructions can advise consultation with a physician for further evaluation and a greater color change can be stated to represent a fertile ejaculate.

The various color chips can also be correlated to other variables in addition to the metabolism rate, e.g., the age of the semen sample; the temperature at which the semen sample was stored, if the sample is not a fresh ejaculate; the temperature at and/or time period over which the test is conducted; and the amount of dilution of the ejaculate, either by the use of a more dilute solution of the dye or by dilution of the ejaculate, e.g., with normal saline, to facilitate collection and measurement. This is done by measuring sperm count and motility of a fresh semen sample, known to be potentially highly fertile, and then assigning the evaluation to the color chip corresponding to the color change achieved when the home test is conducted on that sperm sample where the aforesaid variable or variables are introduced into the test method.

The aforedescribed considerations render the instant invention especially suitable for home use wherein in accordance with a novel kit for practicing the method of the instant invention, a collection means, e.g., a plastic collection tube comparable to a conventional centrifuge tube, is provided for collecting the semen sample. The collection means has indicia thereon, e.g., several lines on the wall of the test tube marked with numbers, indicative of the volume of semen specimen. The kit further includes means for dispensing a measured amount of the dye into the semen-containing collection means, e.g., a pipet containing stored therein, a standard solution of the dye to be reduced by the semen. A predetermined amount of the dye is dispensed into and thoroughly mixed with the semen sample, e.g., from the pipette into the collection tube one drop at a time, the amount dispensed being a predetermined amount based on the volume of semen in the collection tube. For example, the solution of the dye is mixed with the semen by agitating the collection tube. Thereafter, the collection tube is maintained at a preselected temperature, e.g., in a tap water bath at a predetermined temperature for a period of time sufficient to permit a fully fertile semen sample to achieve maximal reduction of the dye. In the preferred embodiment, the tap water bath has an initial temperature which is elevated above room temperature, (30°-50° C., preferably about 46° C. to 48° C.). Conveniently, the water bath is maintained in a drinking water glass, which preferably is insulated by an insulating sleeve supplied with the kit. In accordance with a first embodiment of the invention especially suitable for home determination, after the collection tube has remained in the bath for a predetermined period of time (in accordance with one embodiment, approximately one hour at 48° C.) sufficient to maximally reduce the dye, the test tube is removed from the bath and placed in proximity with a color chart for color comparison with the color chip or chips thereon. The color chart has arrays of color chips gradated in accordance with the expected change in color or shade of the semen sample containing the dye caused by the degree of reduction thereof due to the metabolism of the sperm in the semen sample. A color chip at one end of the array of chips has a color which indicates the lowest possible potential fertility of the semen sample, while another chip at the opposite end of the array indicates the highest possible potential fertility of the semen sample. The chips are preferably on a white background so that the semen sample is always matched against the same white background when the color comparison is made.

In accordance with a second embodiment of the invention, of specific interest to laboratories and clinics, the mixture is examined by spectrophotometry to determine if the dye has been metabolized sufficiently to indicate sufficient sperm count and motility. In accordance with a third embodiment of the invention, again of specific interest to laboratories and clinics, the mixture is monitored by fluorescence microscopy during the reduction of the dye to measure fluorescence, the degree of fluorescence being indicative of the metabolism of the sperm in the sample and thus the count and motility of the sperm.

Resazurin is the preferred dye. Resazurin acetate and methylene blue are alternative reagents. Any other dye which is non-toxic to the viable sperm in a semen sample and which is reducible to a different color or shade, e.g., colorless in the presence of viable metabolizing sperm can be used. In accordance with a preferred embodiment of the invention, the dye solution is made by dissolving the resazurin crystals in water, e.g., in a normal saline solution (0.9 percent), at a concentration which produces a highly colored solution when an aliquot thereof is mixed with a normal ejaculate and which loses a significant amount of that color or changes significantly in a shade upon standing, if the ejaculate is potentially fertile, e.g., 50 mg/100 ml. In conducting the test, typically one drop (0.05 ml) of the 50 mg/100 ml solution is mixed with each milliliter of semen.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
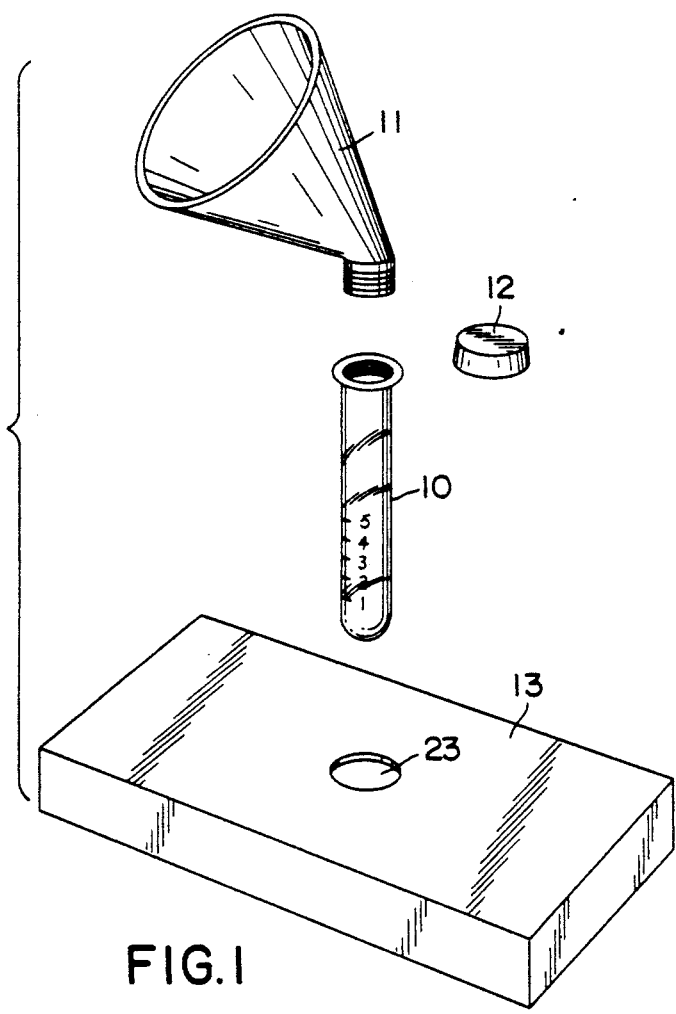
FIG. 1 is a perspective view of a funnel, collection tube with cap and collection tube holder forming part of a novel kit used for practicing the method of the instant invention.
Figure 2:
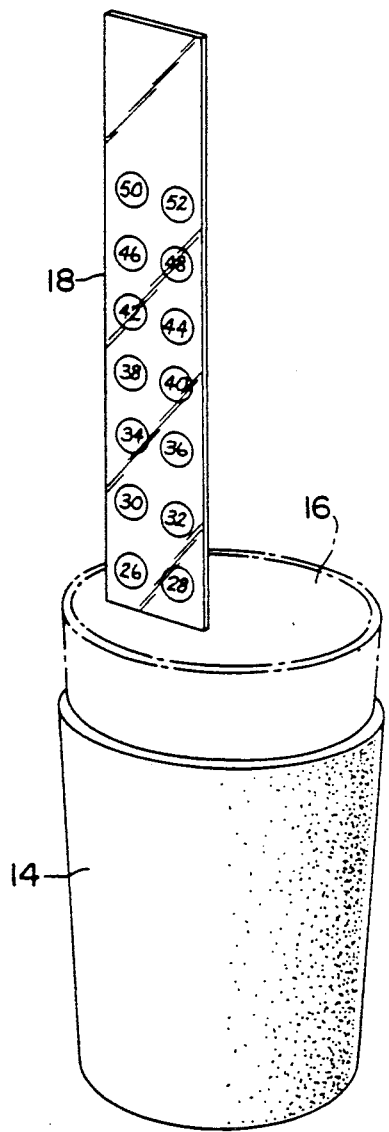
FIG. 2 is a perspective view of a drinking glass used to contain a tap water bath; the drinking glass being contained within an insulating jacket and having a thermometer inserted therein with both the jacket and the thermometer forming part of the kit in accordance with the instant invention.
Figure 3:
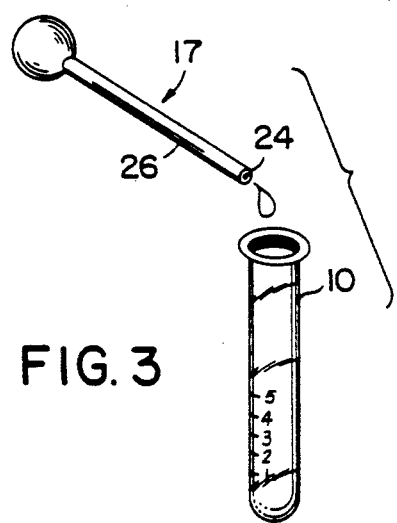
FIG. 3 is a perspective view showing a pipet furnished with the kit of the instant invention, the pipet containing a dye reducible by metabolism of sperm and being dispensed in drops from the pipet into the collection tube.

In accordance with the method of the present invention, an aqueous resazurin (diazoresorcinol) solution is reduced partially or fully by the metabolizing sperm in a semen sample, which typically is one full ejaculate. The collective rate of metabolism of the sperm in the semen sample is a measure of the potential fertility of the semen sample. Solutions of resazurin change color in the presence of metabolizing sperm. These color changes are sufficiently pronounced in aqueous solutions of appropriate concentration so as to be readily apparent when compared to standard color samples, such as, for example, standardized color chips on a chart. Therefore, such color changes are a directed measurement of the fertility of the semen sample.

In accordance with a preferred embodiment of the method, the resazurin solution is prepared by dissolving resazurin crystals in a normal saline solution (0.9 percent) at a convenient concentration, e.g., 50 mg of resazurin per 100 milliliter of saline solution. This forms a reagent dye solution which is initially deep blue or almost black in color. Upon mixing this reagent dye with a semen sample in a ratio of one drop (0.05 ml) of dye solution per approximately one milliliter of semen, the semen sample becomes blue or purple in color. More dilute resazurin solutions produce correspondingly less dramatic color changes which are more difficult to evaluate and more concentrated solutions produce problems in maintaining the desired ratio of dye to semen volume. Over a selected period of time, for example one hour at 48° C., the sample changes color to a redder shade if the sperm therein are sufficiently numerous and mobile to reduce the dye in the sample to a significant extent. The degree of color change in a sample is indicative of the extent to which the resazurin is reduced as a result of the collective metabolizing rate of sperm in the sample and will range anywhere from only a slight shift from its initial shade of blue or purple to a pink shade.

The novel kit used to practice the method of the instant invention relies on the ability of sperm to reduce the selected reagent dye, such as resazurin, and, in the process, effect a change in the color or shade of the reagent dye. In that this change in color or shade is a function of both sperm count and sperm motility, both of which are related to fertility, the test method provides an assessment of the potential fertility of the semen sample containing the sperm. It should be kept in mind that the correlation of sperm characteristics and fertility is not a perfect correlation, because on occasion, pregnancies can result even with low sperm counts and poor sperm motility. Moreover, some men with normal sperm specimens are unable to achieve a pregnancy with their partners. Although there is no known test of sperm potential fertility that is one hundred percent accurate, it is believed that measuring the collective metabolism rate of all of the sperm in an ejaculate may be the most accurate criteria of the potential fertility of the human male donor.

Except when there is complete absence of motile sperm in the semen sample, which is always associated with infertility, the values for sperm analysis based on sperm count and sperm motility against which the home test kit in accordance with the instant invention is compared for accuracy lack definite threshold figures separating fertility from infertility. A sperm count equal to or greater than twenty million sperm per milliliter is generally considered to be in the fertile range, whereas a lower count is considered subfertile. However, there is some disagreement on this level and some laboratories and clinicians use a level of even forty million sperm per milliliter in making a fertile determination. It has been found, however, that twenty percent of the human males with sperm counts below twenty million sperm per milliliters will father a child and as many as fifteen percent of human males with "normal" sperm counts may have some degree of sperm dysfunction that interferes with fertility. Similarly, sperm specimens with below normal motility are not invariably associated with infertility. There is also disagreement over what constitutes the lower limit of sperm motility that can be considered normal, with estimates ranging between forty to sixty percent. Consequently, the current standard for assessing human male fertility is not one hundred percent accurate and in all likelihood is less than ninety percent accurate in categorizing human males as fertile or infertile. In addition, both false positive and false negative results are not uncommon in laboratory sperm analysis. Although the home test method and kit according to the instant invention may reflect some of the inaccuracies inherent in conventional sperm analysis, it could be more accurate than the sperm analysis generally performed by laboratories in that the kit measures collective sperm metabolism. Accordingly, a discrepancy between the results of a home test performed in accordance with the instant invention and the results of a conventional laboratory sperm analysis does not necessarily mean that the home test is erroneous. In the absence of a more precise test for human male fertility, the standard laboratory sperm analysis is the only standard comparison now available for the home kit in accordance with the instant invention.

A primary advantage of the home test kit is that it will encourage men having a low assessment of potential fertility to seek medical attention while those who have a high assessment of potential fertility will have an indication that lack of fertility may reside elsewhere. Generally, in a situation where the test kit indicates a high assessment of fertility potential, a couple would be well advised to attempt to conceive for a period of four months before seeking medical advice on their fertility.

There are a number of benefits to utilizing the test kit in accordance with the instant invention, one of which is that the individual will be able to assess the potential fertility of his sperm specimen in the privacy of his home. Another benefit is that men undergoing treatment for infertility can utilize the home test kit to monitor changes in sperm metabolism to determine whether or not the treatment is effective. Another advantage is that the evaluation can always be made with a fresh semen sample and the sperm is not exposed to cold temperatures which can be encountered on the way to the laboratory. Another advantage is that the home test kit will lower the cost of human male fertility evaluation in that it is less expensive for an individual to utilize the home test kit than to have his sperm analyzed at a laboratory. The test kit also can be used by a doctor who does not have ready access to or who does not choose to utilize the facilities of a laboratory equipped to conduct a conventional sperm analysis. The test kit also can be used to evaluate the fertility of stored, e.g., liquid nitrogen frozen sperm. The frozen sperm sample would be thawed to room temperature prior to mixing with the appropriate volume of dye.

Considering now more specifically the test kit in accordance with the instant invention and the use thereof to practice the method of the instant invention, it is seen that the kit comprises a plurality of relatively simple components which can be packaged in a box. The components include a collection tube 10, a funnel 11, a cap 12, a support 13 for the test tube 10, an insulating jacket 14 for a drinking glass 16 (not supplied in kit), a pipet 17 containing the dye to be reduced by the sperm in the semen sample, a disposable thermometer 18 and a color chart 19 with which the sample in the test tube is compared in the presence of light from an ordinary incandescent lamp 21.

The person who wishes to test his fertility utilizes the aforementioned components of the kit in accordance with the following procedure. After abstaining from an ejaculation for a period of at least seventy-two hours, an ejaculate is collected in the tube 10 using the funnel 11 screwed onto the threaded mouth thereof to guide the ejaculate into the tube. In order to increase the convenience of collection, the axis of the funnel 11 is at an angle of forty-five degrees with respect to the axis of the tube 10. The tube 10 with the funnel 11 therein is then supported vertically by inserting the tube 10 into a hole 23 in the support 13 which support may be, for example, a cardboard box and maintained in that position for twenty minutes at room temperature, to permit the semen in the funnel 11 to drain into the tube 10. During that twenty minute period, the sperm specimen will become more liquid. It is not necessary for all of the semen to drip into the tube 10, and a small amount can stay behind in the funnel 11.

After a substantial portion of the semen has drained into the tube 10, the funnel 11 is removed and discarded. The tube 10 has a number of gradations or lines inscribed on the side thereof, e.g., representing milliliters or fractions of a fluid ounce, indicated by the numerals "1", "2", "3", "4", "5". The level of the semen sample in the tube 10 is compared to the line on the test tube nearest the upper surface of the semen specimen. This indicates the volume of the specimen in the tube or other unit volume of the sample. The numeral on the side of the tube 10 indicative of the volume of the semen sample determines the number of drops of dye solution to be dispensed from the pipet 17 into the semen sample.

The pipet 17 containing the dye solution is preferably packaged in a conventional plastic wrapper and has the dye solution sealed therein. To dispense the dye solution, the small diameter end 24 of the pipet 17 is snipped off with a pair of scissors and a couple of drops of the dye solution are expelled from the pipet 17 and discarded, e.g., into a toilet bowl, in order to discharge any air from the tubular portion 26 of the pipet. The pipet 17 is then aligned with the top of the tube 10 and slowly squeezed to dispense the appropriate number of drops therefrom corresponding to the numeral aligned with the gradation on the test to which the top of the semen sample most closely aligns. For example, if the level of semen rises to the numeral "2", then two drops of a 50 mg/100 ml dye solution are dispensed from the pipet 17; if the level in the test tube 10 rises to the numeral "3", then three drops of dye are dispensed from the pipet, and so forth. If a more dilute dye solution is employed, an appropriately larger number of drops of the dye solution are dispensed. The cap 12 is then placed on the test tube 10 to close the test tube.

The next procedure to be followed in conducting the test is to insert a standard 8-ounce drinking glass 16 into the insulating jacket 14. The insulating jacket 14 furnished with the kit is of a size which surrounds the cylindrical surface of the glass 16 as well as underlying the bottom of the glass. The test bath is prepared by filling the drinking glass approximately two-thirds full with hot, but not boiling, tap water. The plastic strip thermometer 18 is then inserted into the water with all of the numbers submerged. The plastic strip thermometer is preferably a conventional disposable thermometer and indicates temperature by a green circle which appears just above the numeral corresponding to the temperature of the bath. In accordance with the instant invention wherein the dye is resazurin, the initial temperature of the bath should be about forty-six degrees to forty-eight degrees celsius. If the green circle is above fifty degrees centigrade, an appropriate amount of cooler water should be added after discarding some of the water in the glass. When the correct temperature is achieved, i.e., 46°-48° C. in accordance with the preferable dye used in the instant invention, the strip thermometer 18 is withdrawn from the bath and discarded.

Figure 4:
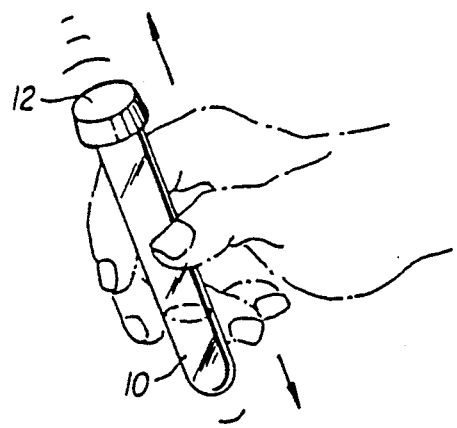
FIG. 4 is a perspective view of the collection tube being agitated.

As is seen in FIG. 4, the tube 10 with the cap 12 in place is then agitated by shaking the test tube three or four times in order to thoroughly mix the semen and the dye solution. If the dye solution used is a 50 mg/100 ml resazurin solution as previously described, the specimen will be deep blue or purple after mixing.

Figure 5:
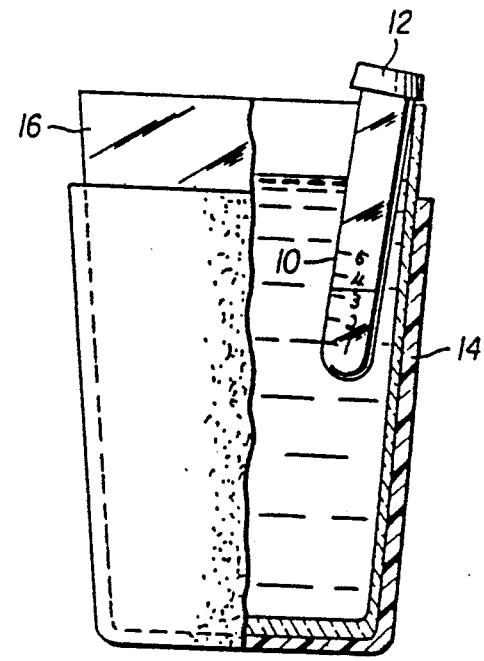
FIG. 5 is a side view showing the collection tube floating in the bath of FIG: 2.

As is seen in FIG. 5, the tube 10 is then placed in the bath of tap water with the cap end of the test tube up. The tube 10 will partially float with the upper portion resting against the side of the glass 14. The person conducting the test then writes down the time the tube 10 was inserted in the bath and leaves the test tube in the bath for a period of one hour. During this time, the tube is in the bath and the glass 14 is maintained on a flat surface away from open windows or air conditioners which might excessively cool the bath, viz., below about 34° C. In a very cool room, it may be necessary to replace the water with warmer water during the hour holding period to ensure that the test mixture does not become too cool.

After one hour has passed, the test tube 10 is removed from the bath and shaken two or three times. The test result is determined by comparing the color of the specimen in the test tube 10 with the various colors on the color chart 19 while the color chart and test tube are bathed in daylight or light from a conventional incandescent lamp 21. Fluorescent light ordinarily can not be used because it often distorts color reflected from the chart and specimen. The color chart 19 has a plurality of color chips 31a-31k positioned adjacent one edge thereof on a white background 32. The color chart 19 is preferably divided into a low fertility region 33, indicated by a minus sign or a designation "negative", and a high fertility region 34, indicated by a plus sign or a designation "positive". Since the test tube 10 is transparent, the color of the semen-dye mixture can be viewed against the white background 32 of the color chart 19 and compared to the various chips 31a-31k, which range in color from plum purple to bright pink. In making an assessment as to the potential fertility of the sperm, the chip among color chips 31a-31k which most closely matches the color of the semen-dye mixture is indicative of the sperm metabolism of the sample. If the chip among color chips 31a-31k which is matched is in the positive region 34, then the subject knows that at the time the semen sample was taken his potential fertility was high, whereas if the chip is in the low region 33, the subject knows that at the time his semen sample was taken his potential fertility was low. No change in color is strongly indicative of infertility.

Figure 6:
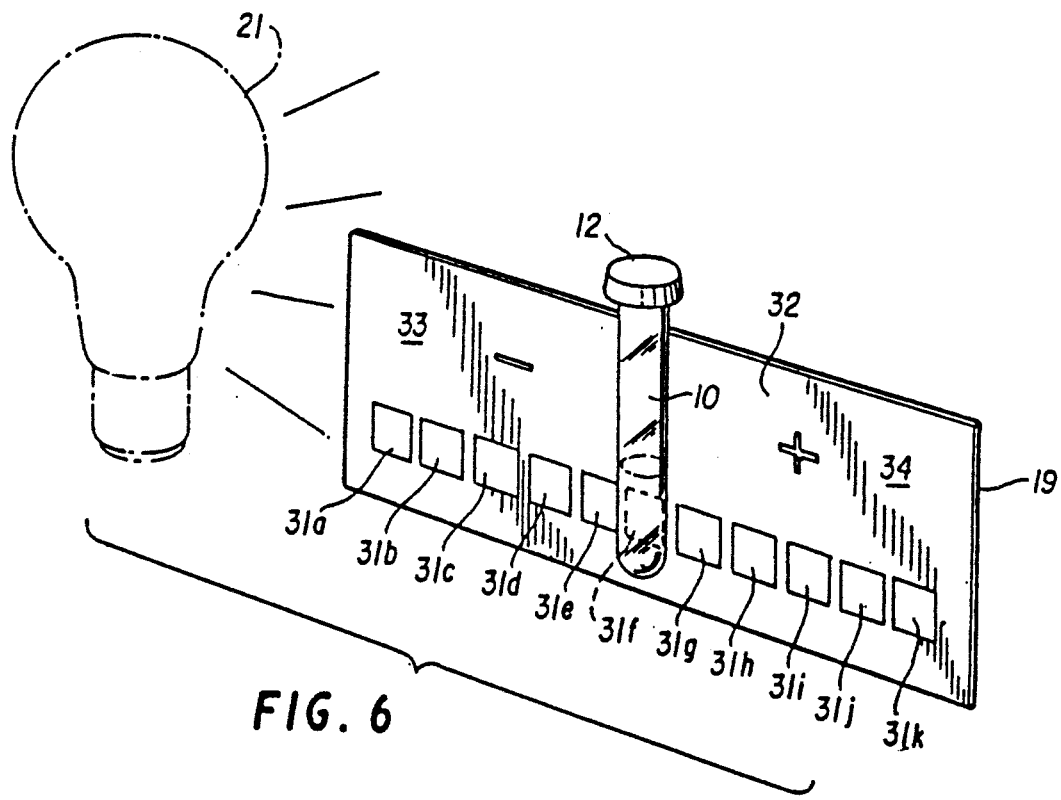
FIG. 6 is a perspective showing the semen and dye mixture being compared to a color chart in the presence of incandescent light after the collection tube has been removed from the bath.
Figure 7:
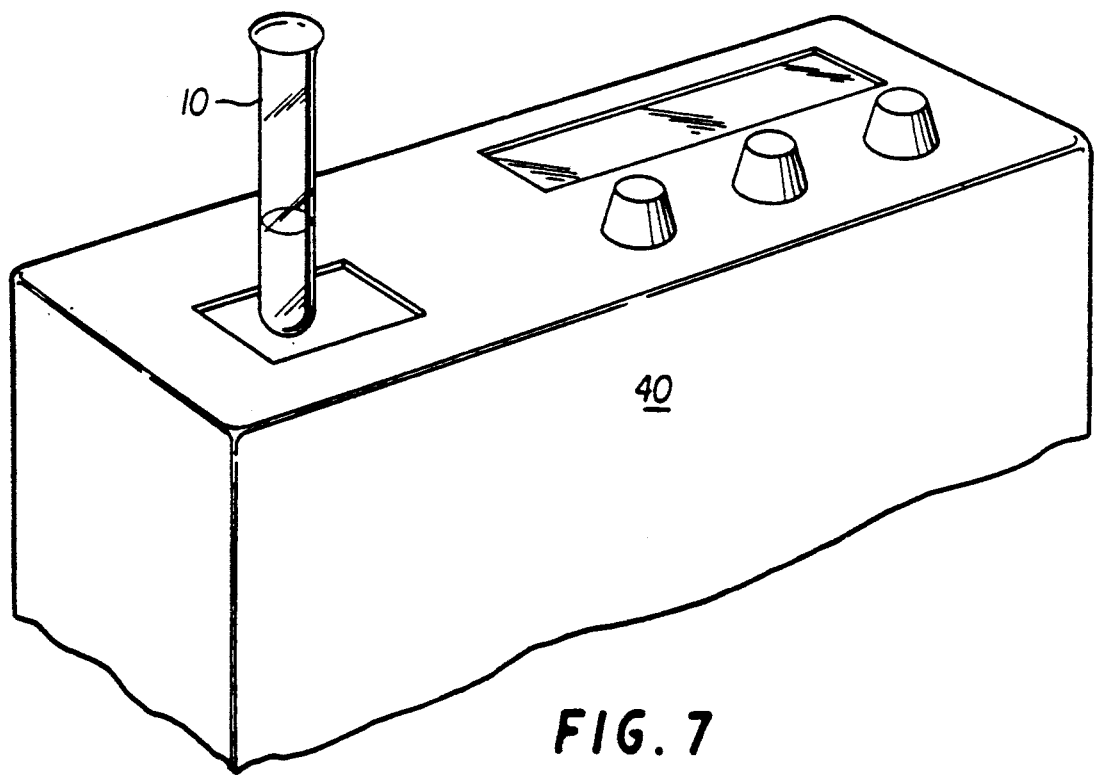
FIG. 7 is a diagrammatical view of alternative embodiments of the invention showing a semen and dye mixture in a cuvette being examined by a device such as a spectrophotometer, colorometer, or fluorometer to determine the extent to which the dye has been reduced by sperm in the semen sample.

Referring now to FIG. 7, wherein alternative methods of examining semen samples for fertility are diagrammatically illustrated, it is seen that the semen sample, instead of being visually examined as shown in FIG. 6, is examined by a device such as a spectrophotometer, colorometer or fluorometer 40. By utilizing a suitable test tube 10, which is in the form of a cuvette, readily insertable into the device, an automatic determination can be made as to whether or not the semen sample is capable of fertilizing an egg.

Assuming that the device 40 is a spectrophotometer, the semen sample which is either diluted or undiluted in distilled water is placed in the spectrophotometric cuvette 10. Exemplary of a spectrophotometer which can accomplish the aims of the instant invention is the Perkin-Elmer Lamda III UV/VIS spectrophotometer which is calibrated automatically and reads specimens in the cuvettes individually. Negative semen samples indicating infertility give a maximum absorbency at a wavelength of 600 nanometers. In a negative reading, the initial and final color of the semen sample is dark blue. A positive semen sample has an initial color of dark blue but changes to reddish pink and provides only baseline absorbency. The device 40 could be either a spectrophotometer or an equivalent colorometer since these instruments are interchangeable operating on the same physical principle so as to produce the same results.

If the device 40 is a fluorometer, such as the digital fluorometers Turner Models 112 and 450, quantitative analysis of fluorescence is accomplished during the chemical reaction in which resazurin which is dark blue in color is reduced by cell metabolism to resorufin which is pink in color.

Figure 8:
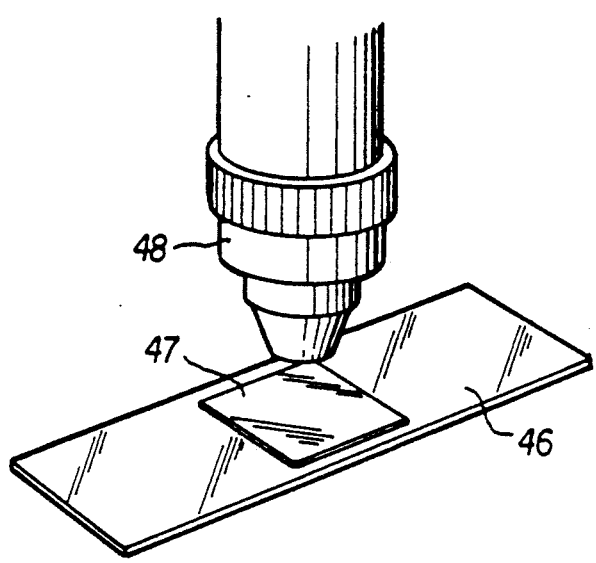
FIG. 8 is a perspective view of an additional embodiment of the invention showing a sample of a semen and dye mixture being examined with a fluorescent microscope.

Referring now to FIG. 8, there is shown an additional embodiment of the invention wherein the semen sample is analyzed by a fluorescent microscope 48 rather than being analyzed visually as is shown in FIG. 6. With this approach, a portion of the semen sample is placed on a microscope slide 46, covered with a cover slip 47 and viewed through a fluorescent microscope 48 which may be, for example, a standard Zeiss fluorescent microscope. If the semen sample is positive for fertility, it will appear red when a filter for a fluorescent stain, such as Rhodamine, is used. Only a dark background is visible when the filter for Fluorescein is used. Fluorescein is another fluorescent stain that fluoresces at a different wavelength than Rhodamine. If the population and motility of the sperm in the semen sample is not high enough to reduce the dye, then there will be no fluorescence when the sample being reviewed is viewed through a filter for Rhodamine or a filter for Fluorescein.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A test kit for determining the potential fertility of a semen sample of a human male, the test kit comprising:
   a container with collection means for receiving the semen sample, comprising a gradation thereon for determining the volume of the semen sample;
   a reagent dye which is capable of being reduced in the presence of metabolizing sperm from one colored state to another colored state;
   a dispensing device for dispensing a measured amount of the reagent dye;
   means for maintaining a mixture of the dye and semen sample at an elevated temperature; and
   a color chart comprising a plurality of color samples corresponding to the color change affected in corresponding mixtures of the dye and sperm samples of known varying number of motile sperm cells per ml, including an infertile sperm sample.

2. A test kit of claim 1, wherein the collection means further comprises a funnel for directing the semen sample into the collection means.

3. A test kit of claim 1, wherein the dispensing means comprises a pipet in which an aqueous solution of the reagent dye is stored and which has means for dispensing discrete drops of the reagent dye into the container, the number of the drops dispensed corresponding to a number aligned with the gradation on the test tube with which the semen sample aligns.

4. A test kit of claim 1, wherein the means for maintaining a mixture of the dye and semen sample at an elevated temperature comprises a container for holding the collection means and means for insulating the container for holding the collection means, the container for holding the collection means providing a bath for warming the collection means and its contents upon immersing the collection means therein; and
   a thermometer for measuring the temperature of the bath upon immersing the thermometer in the bath, whereby the temperature of the bath can be readily adjusted with tap water.

5. The kit of claim 4, wherein the thermometer is a disposable thermometer.

6. The kit of claim 5, further comprising support means for the collection means, the latter being insertable in the support means so as to stand vertically while it receives the semen sample and drops of the dye.

7. The test kit of claim 1, wherein the reagent dye is a solution of resazurin.

8. The test kit of claim 1, wherein the color chart includes a fertile area with a plurality of color samples and an infertile area with a plurality of color samples, the samples being mounted on a white background, whereby the color of the dye-semen sample mixture in the tube can be compared with the color samples while positioned against the white background.

* * * * *